United States Patent [19]

De Ros et al.

[11] Patent Number: 5,156,074
[45] Date of Patent: Oct. 20, 1992

[54] WELL FORMING APPARATUS

[75] Inventors: Angelo De Ros, Bresso; Luigi Cavenaghi, Milan, both of Italy

[73] Assignee: Gruppo Lepetit S.P.A., Milan, Italy

[21] Appl. No.: 370,150

[22] Filed: Jun. 22, 1989

Related U.S. Application Data

[63] Continuation-in-part of Ser. No. 230,655, Aug. 5, 1988, abandoned, which is a continuation of Ser. No. 122,558, Nov. 13, 1987, abandoned, which is a continuation of Ser. No. 837,433, Mar. 7, 1986, abandoned.

[30] Foreign Application Priority Data

Mar. 8, 1985 [IT]  Italy ................................ 21051 B/85

[51] Int. Cl.⁵ ............................................. B26D 1/06
[52] U.S. Cl. ........................................ 83/100; 83/167; 83/620; 83/633; 83/919
[58] Field of Search ..................... 83/24, 55, 100, 167, 83/599, 633, 620, 919; 408/58

[56] References Cited

U.S. PATENT DOCUMENTS

| | | | |
|---|---|---|---|
| 2,463,455 | 3/1949 | Dann | 408/58 X |
| 3,472,101 | 10/1969 | Tanaka | 83/633 X |
| 3,600,722 | 8/1971 | Farris | 83/167 |
| 3,631,575 | 1/1972 | Farris | 83/599 |
| 3,863,533 | 2/1975 | Hurn | 83/100 |
| 4,354,406 | 10/1982 | Brun et al. | 83/24 |

FOREIGN PATENT DOCUMENTS

0086706  8/1983  European Pat. Off. .
0159950  10/1985  European Pat. Off. .

*Primary Examiner*—Frank T. Yost
*Assistant Examiner*—Kenneth F. Peterson
*Attorney, Agent, or Firm*—Michael J. Sayles

[57] ABSTRACT

The present invention relates to an apparatus which is able to form a desired number of wells in gelatinous media, as for example agar-based media contained in dishes or plates such as the normal microbiological culture dishes or plates.

2 Claims, 8 Drawing Sheets

5a

5d

5b

5c

WELL FORMING APPARATUS

CROSS-REFERENCE TO RELATED APPLICATION

This is a continuation-in-part of application Ser. No. 230,655, filed Aug. 5, 1988, now abandoned, which is a continuation of application Ser. No. 122,558, filed Nov. 13, 1987, now abandoned, which is a continuation of application Ser. No. 837,433, filed Mar. 7, 1986, now abandoned.

The present invention relates to an apparatus which is able to form a desired number of wells in dishes or plates containing gelatinous culture media, such as agar-based media like the normal dishes or plates used for microbiological cultures and assays.

The apparatus of the invention is able to simultaneously form a desired number of wells with a limited number of simple operations. The well is formed in the agar, or other gelatinous matrix of similar consistency (hereinafter for the sake of convenience called "agar"), by the cutting action of hollow stainless steel borers which penetrate the entire depth of the agar. The plug of agar that thus fills into the distal portion of the hollow borer is removed and collected in an apposite chamber by applying aspiration (vacuum). The dish or plate with the wells formed in the agar is then ready for use, or can suitably be stored until the time of use.

A wide variety of assay and analysis methods based on the diffusion of reagents and substrates on agar or similar matrices are known. For instance, a traditionally widely used type of assays relates to the production of antibiotics by unknown microorganisms, or to the microbiological activity of a known antibiotic. In general, these methods use a microorganism susceptible to the antibiotic to be assayed, which test organism is grown in the nutrient medium that fills, or will be used to fill, the dish or plate. An appropriate solution of the test substance is then placed on the surface of the medium on the plate and, after the requisite incubation period, the diameter of the zone of inhibition produced by the test substance is measured and correlated to the concentration of the antibiotic substance.

Substantially the same technique has more recently been successfully applied to evaluation methods based on antigen-antibody reactions and formation of antigen-antibody complexes which are commonly known as immunodiffusion techniques.

Two methods are normally used for placing the test substance onto the dish or plate (i.e. the support containing the agar-based culture medium): one method includes to place onto the surface of the agar in the dish or plate a reservoir containing, or apt to contain, a solution of the test substance, such as paper discs which have been dipped in a solution of the test substance or hollow cylinders apt to contain a solution of the test substance; the other method is to place the solution of the test substance into a well preformed in the agar.

On laboratory scale, these latter wells are normally obtained by the manual use of a single hollow borer. This technique suffers from many drawbacks which includes that of having to remove the agar plug manually from the hollow borer.

The present invention relates to an apparatus, particularly suitable for use on laboratory scale, which permits simultaneous boring of a desired number of wells in a base-layer of agar or material of similar consistency contained in dishes or plates, with simultaneous removal of the agar plugs which form.

The advantages deriving from the use of such an apparatus will be immediately evident to persons of ordinary skill in the art.

Such advantages include:
a) ease and rapidity of execution
b) uniformity of the dimensions of the bored wells and of their relative distances
c) considerable time-saving in the preliminary procedures called for when analyzing a large number of samples on a laboratory scale.

DETAILED DESCRIPTION OF THE PRESENT INVENTION

Figure 1:
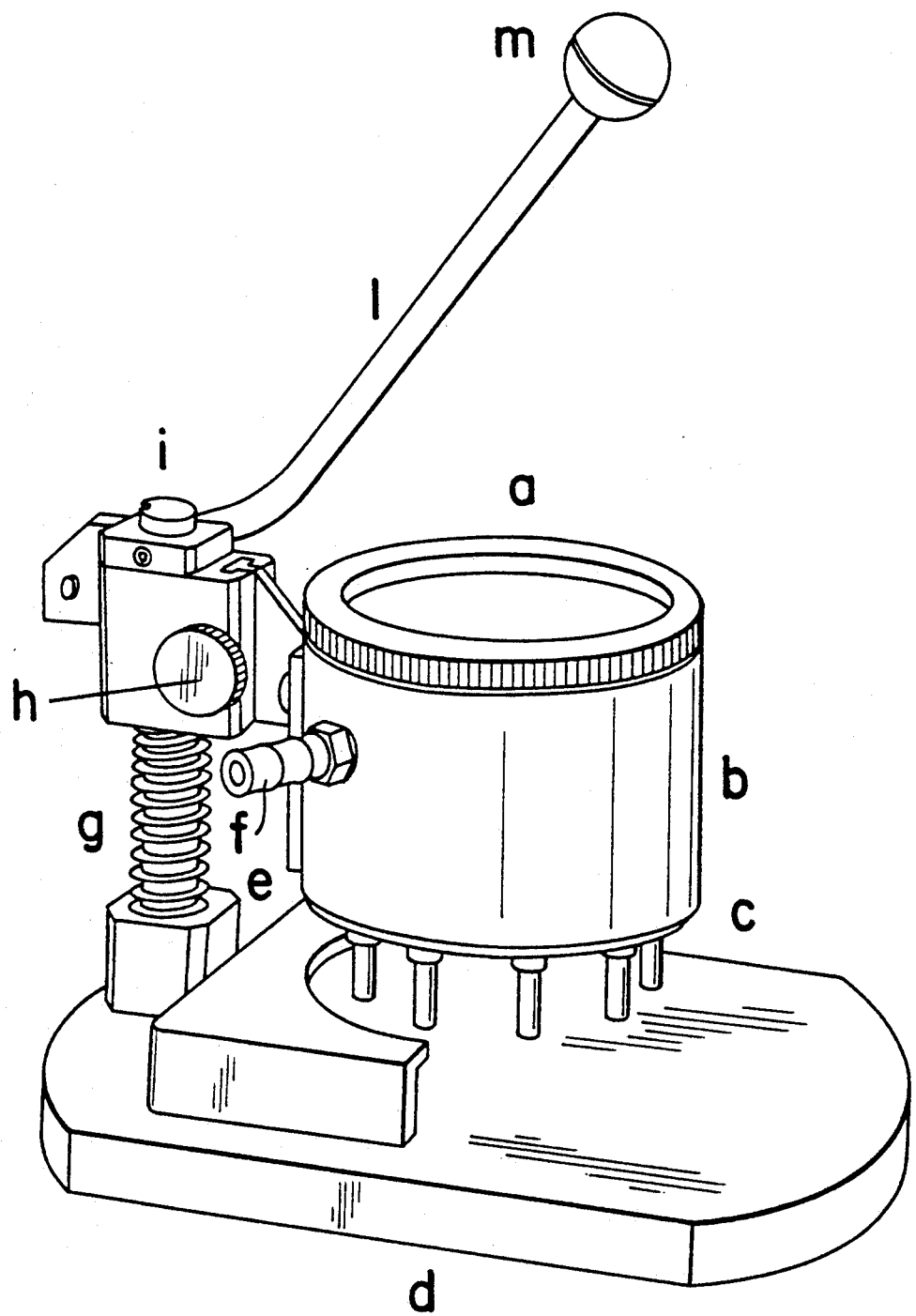
FIG. 1 shows a side view of a preferred embodiment of the present invention.

FIG. 1 illustrates an example of embodiment of the apparatus according to the invention, it includes:
I) a central body carrying the immovably affixed hollow borers, which are of predetermined dimensions and at a predetermined distance one from the other (see for example detail 1b of FIG. 1, FIG. 2 and FIG. 4B)
II) a means for aspirating the agar plugs removed from the agar contained in the dish or plate, consisting of a chamber (as for example the chamber shown in detail in the top view of FIG. 3) connected to a vacuum system and comprising a collecting portion for the agar plugs which are removed (as exemplified in FIG. 3, detail 3b)
III) baseplate and support and housing means for the central body (as exemplified in detail 4a in FIG. 4A)
IV) means for actuating the central body by lowering and for the automatic return to the raised position (such as the means represented by the lever 4c and the spring 4b in FIG. 4A)
V) means for positioning the dish or plate (4d) on the baseplate so as to maintain the dish or plate in a correct position beneath the central body (an illustrative representation is given in FIG. 4A).

Figure 2:
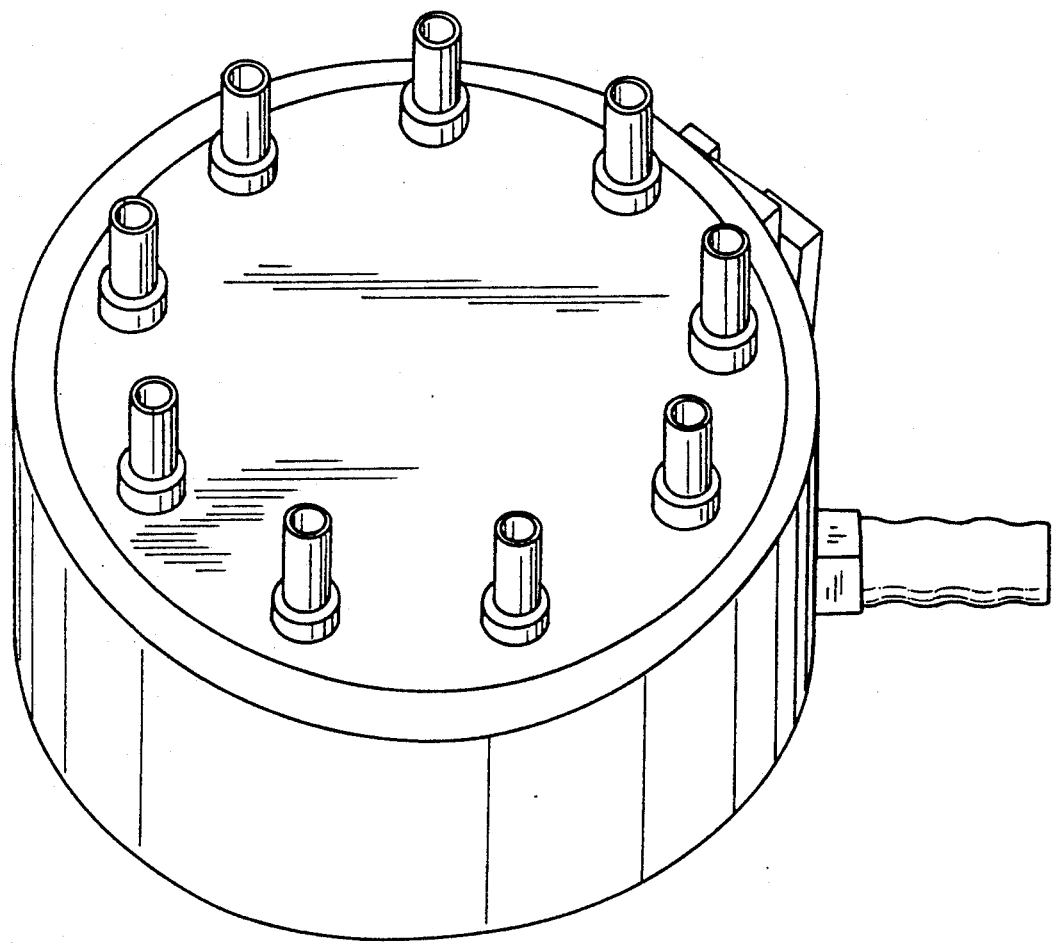
FIG. 2 shows a detailed view of the bottom of the central body and hollow borers.
Figure 3:
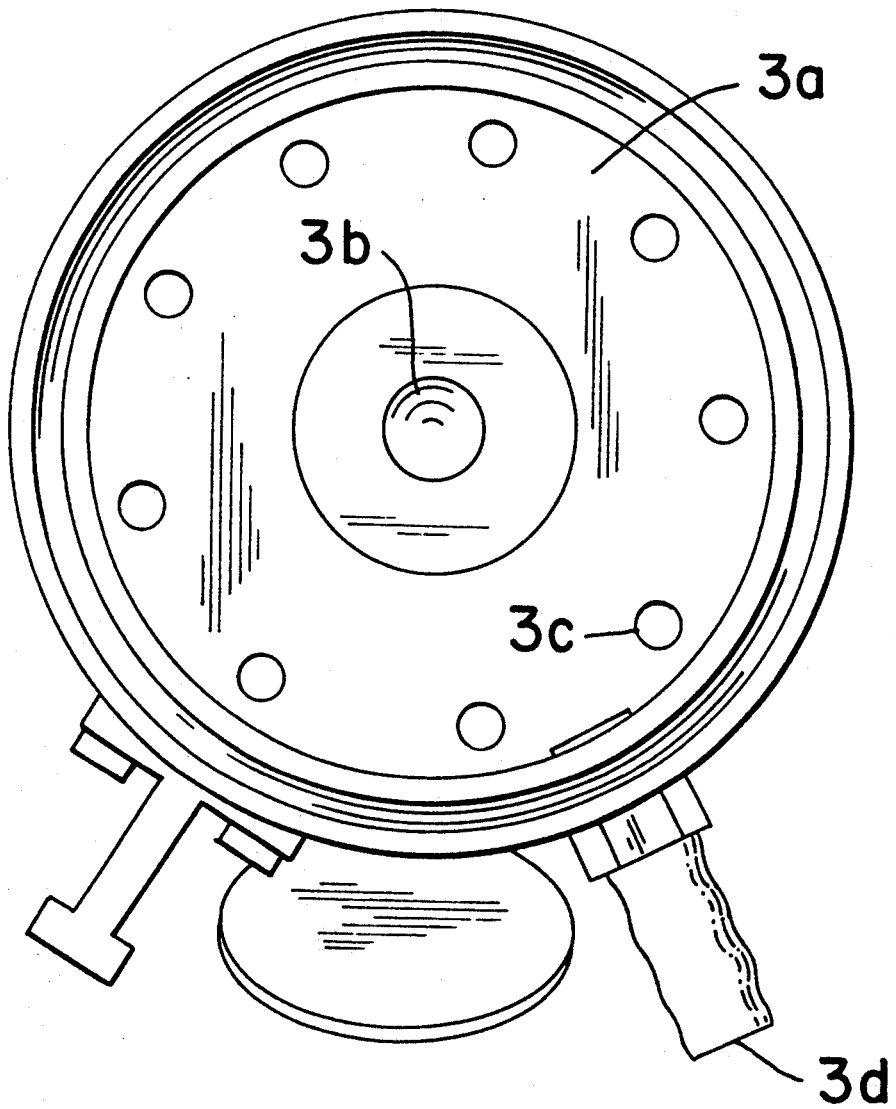
FIG. 3 shows an elevated cross-sectional view of the central body.

With reference to FIGS. 1, 2 and 3, the dimensions of the central body depend on those of the dish or plate that is utilized, and are such as to house the preselected number of hollow borers of predetermined dimensions and at predetermined distances. The dimensions of the hollow borers, and in particular of the distal portion thereof intended to bore out the well in the agar, depend not only on the dimensions of the dish or plate but also on the amount of the test substance (generally a solution or suspension) which they will contain; such dimensions can be selected for example from a range of internal diameters of from 1 mm to 20 mm, and preferably will be 5-9 mm. Preferably, the central body which houses the hollow borers has a truncated cone shaped internal cavity (as shown in FIG. 3) into which debouch the conduits of the proximal portions of the hollow borers (3c), which central cavity, after it has been closed by means of the relative cover (as shown for example at 5b in FIG. 5), can act as an aspiration and collection chamber for the removed agar plugs.

The central body also presents a fitting (3d) for connection to the aspiration means, which is generally a normal central vacuum system or vacuum pump able to provide a force of aspiration sufficient to aspirate the agar plugs from the point of their formation and draw them into the collection chamber. In general, the vacuum values available in laboratories (5-50 mmHg) are adequate for this purpose. In any case, the value of the vacuum required depends on the number and dimensions of the wells simultaneously bored by the apparatus, and can readily be determined by preliminary tests on the basis of the results of the present disclosure.

The central body can advantageously be constructed from plastic material (as for example PVC), but the use of metal is also a viable possibility.

Figure 6:
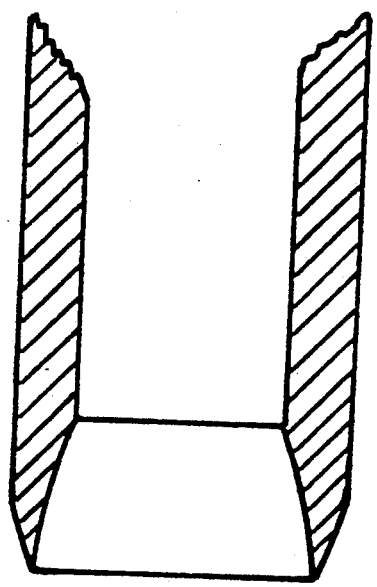
FIG. 6 shows a side view of the distal portion of the preferred hollow borer.

The hollow borers, on the other hand, are constructed from stainless steel, and their terminal blades are precision sharpened. As the wells are generally required to be circular, the hollow borers have as a rule a circular cross-section. A preferred type of hollow borer is the borer whose distal portion is shown in FIG. 6.

Figure 4A:
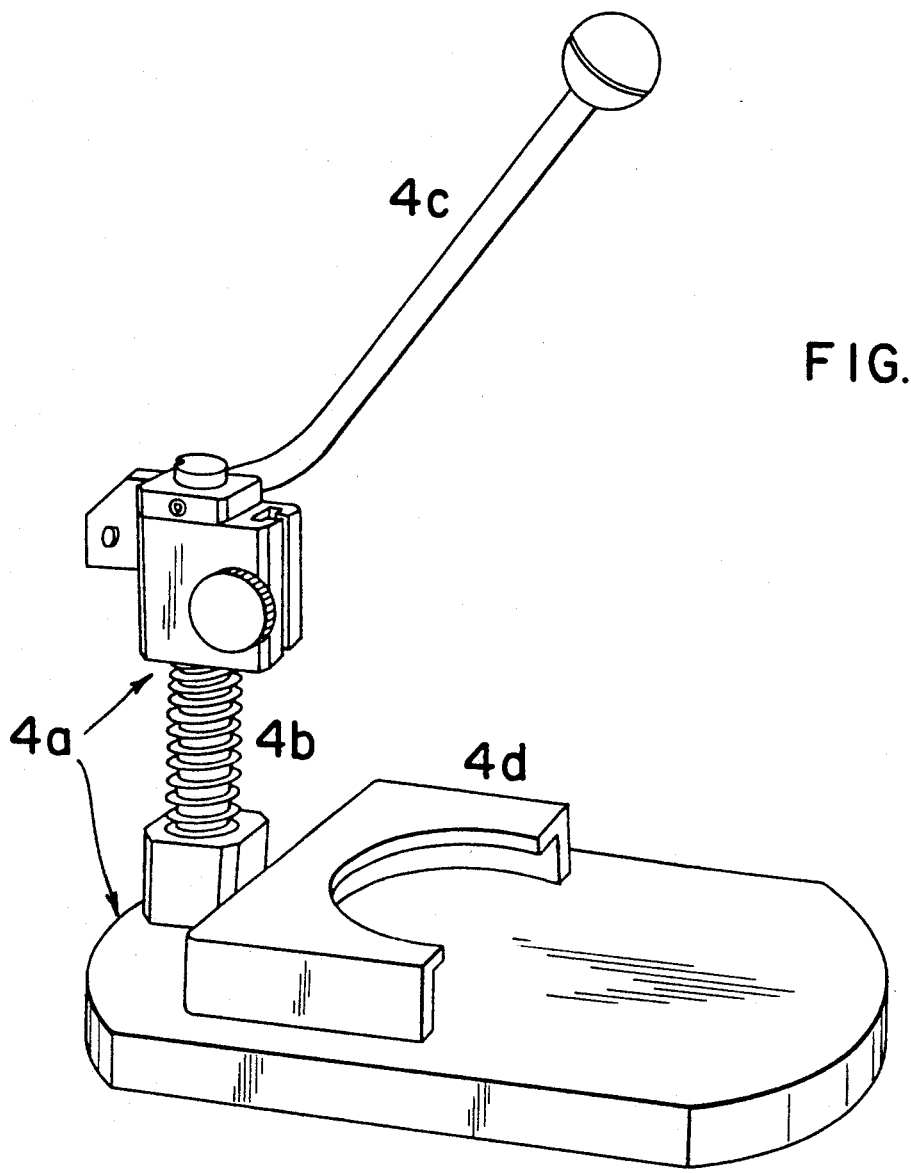
FIG. 4A shows a side view of the base plate, dish positioner, means for supporting the central body, and means for lowering and raising the central body.
Figure 4B:
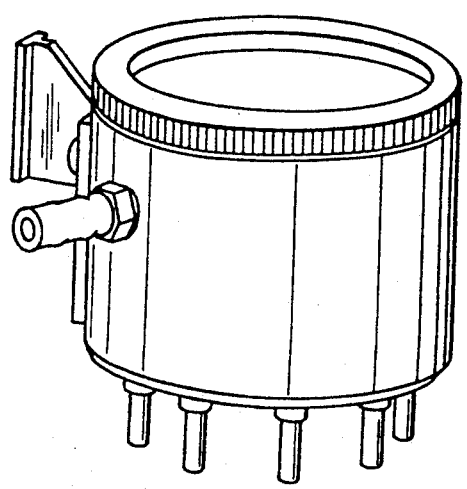
FIG. 4B shows an elevated side view of the central body.

As illustrated in FIG. 1 and by detail in FIG. 4B, the central body is closed by means of a screw-cover and a vacuum seal ring. The screw-cover is preferably transparent in order to permit trouble free visual inspection of the internal portion of the aspiration chamber. The screw-cover is preferably made of plastics, for example plexiglas, but can also be made of glass. Advantageously, said cover has a dead hole on its edge to which a cover-release means may be adapted (an exemplifying illustration of which is reported in details 5b and 5c of FIG. 5), which can cooperate in opening the cover, should such opening otherwise be problematical.

Figure 5A:
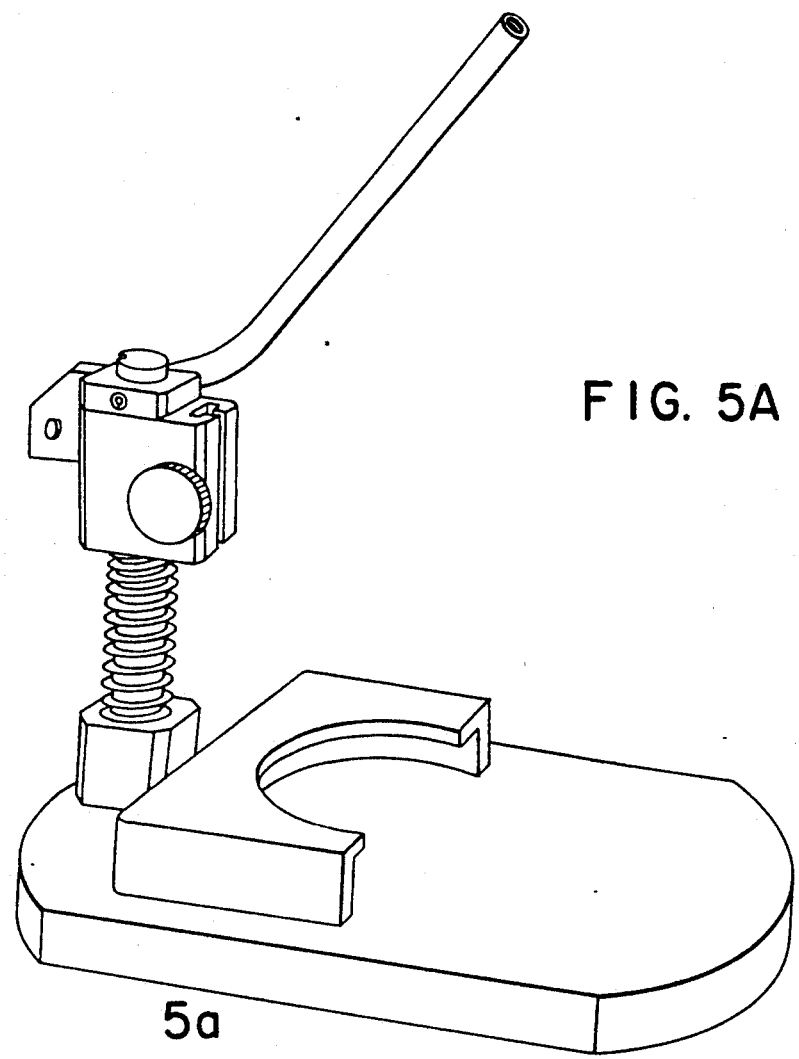
FIG. 5A shows a side view of the base plate, dish positioner, means for supporting the central body, and a preferred embodiment of the means for lowering and raising said central body.
Figure 5B:
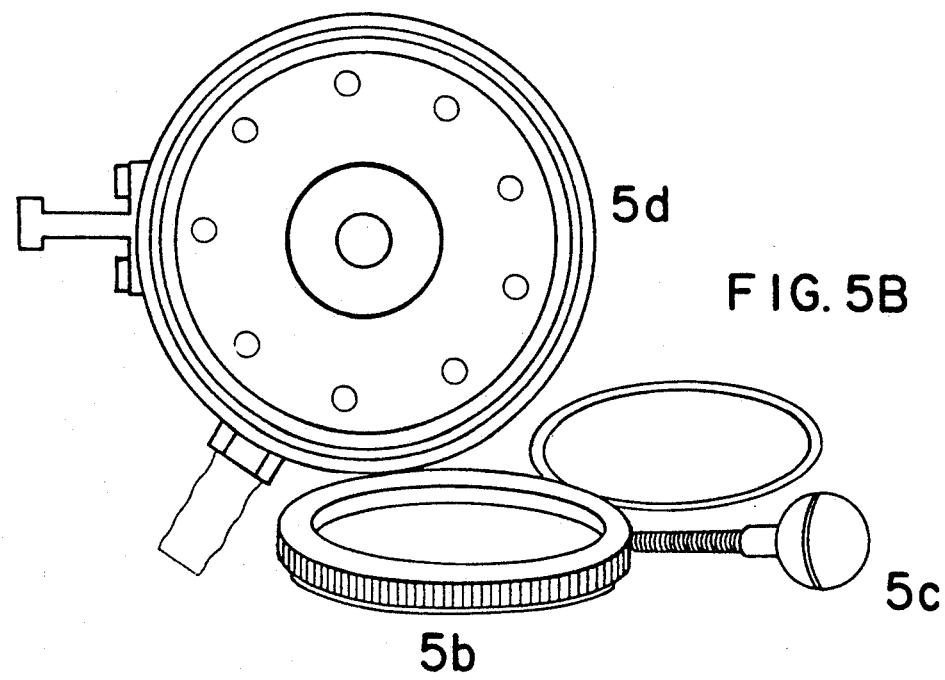
FIG. 5B shows a preferred embodiment of the central body in a disassembled state.

This cover-release means, see detail 5c, FIG. 5, is conveniently formed of the ball-grip of the actuating level (4c) which carries a rod of suitable length and has a size such that it can be housed into said lever which, at least in its initial portion, is consequently hollow.

According to a feature of the present invention relating to an embodiment thereof suitable for use on laboratory scale, the central body is actuated by means of a lever which, when depressed, causes the lowering of the central body and thus the penetration of the agar without any motion substantially perpendicular to the path of penetration of the borers to the agar gel by the cutting end of the hollow borers so as to bore out wells of predetermined dimensions. The return of the lever and thus of the central body to its raised (or rest) position can in this case be effected by the action of a mechanical spring which extends after being compressed by the depression of the actuating lever.

Figure 7:
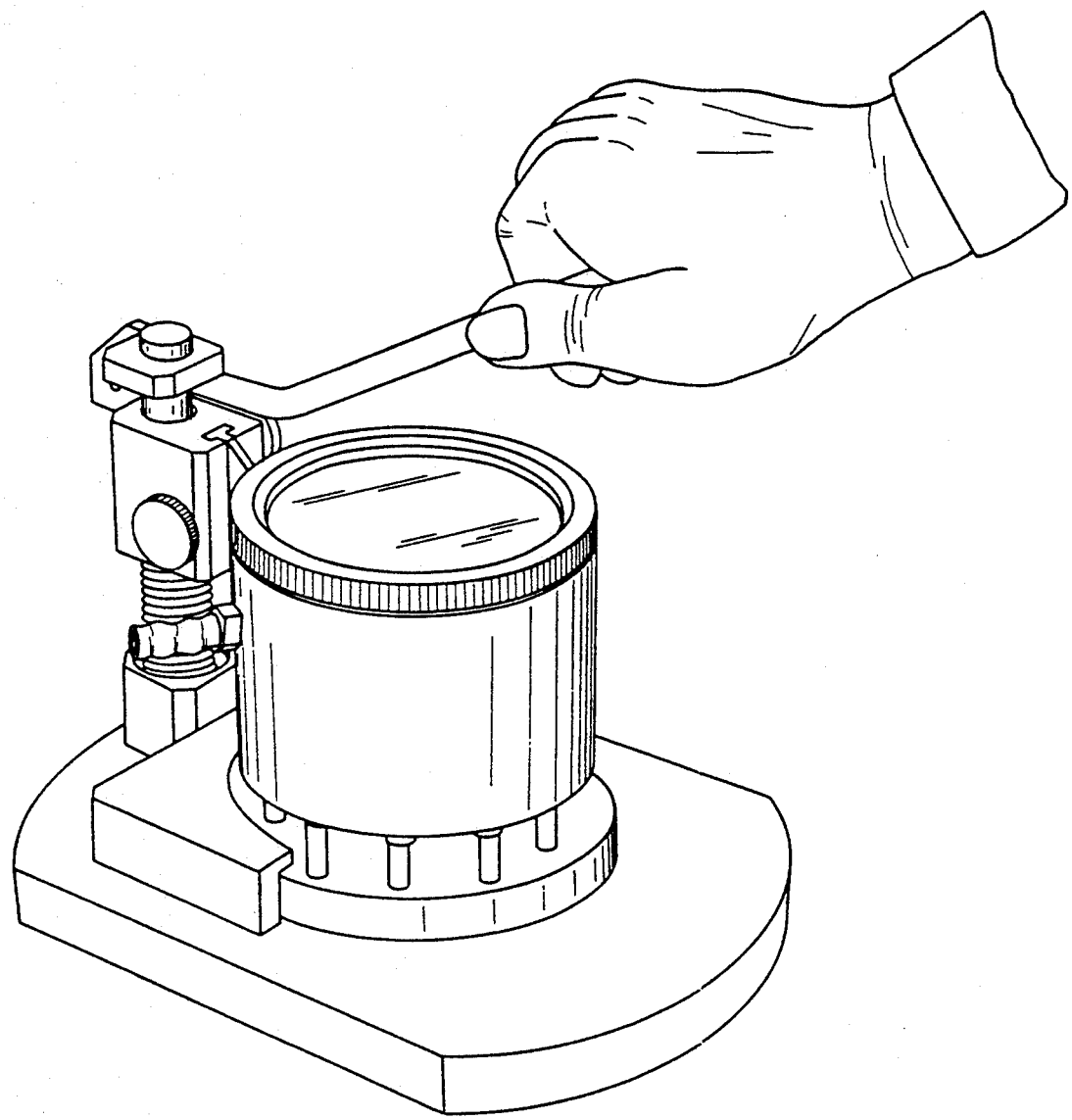
FIG. 7 shows an elevated side view of the baseplate and dish positioner supporting a Petri dish in a stationary position while the central body is being lowered in order to allow the hollow borers to contact the gelatinous matrix thereby forming wells within its surface.

FIG. 1 shows the aforesaid apparatus of the invention in the rest position, and FIG. 7 shows it in its lowered or "working" position.

Figure 8:
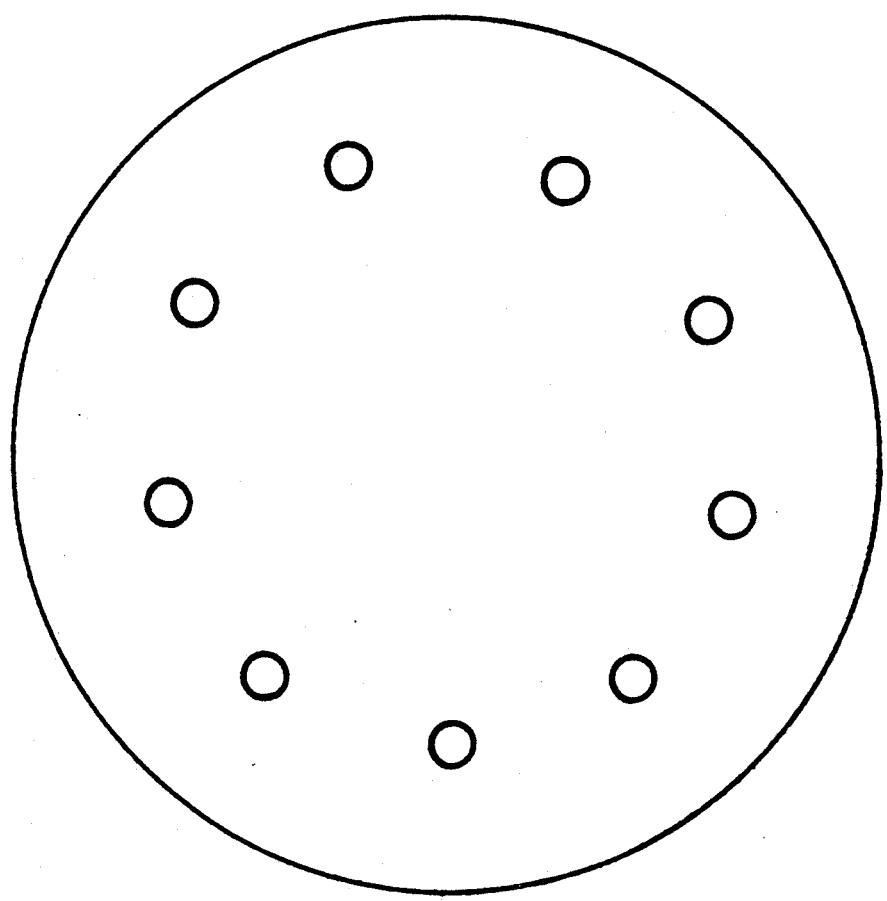
FIG. 8 shows an elevated view of a dish or plate with wells bored in it.

An example of a dish or plate with wells bored by the apparatus of the invention is shown in FIG. 8.

Particularly preferred for applications on laboratory scale is the apparatus shown in FIG. 1, which incorporates:

a: a transparent plastic screw-cover b: a central PVC body which carries the stainless steel borers (c), a fitting for connection to the hollow aspiration system (f) (vacuum pump) and an internal hollow chamber which has, in its lower portion, a preferential zone for collecting the agar plugs (aspiration cylinder)

c: hollow stainless steel borers suitably shaped at their ends in contact with the agar so as to bore out a well without agar residues on the bottom of the plate and with falls free from unevennesses d: a baseplate e: means for positioning the dish or plate (positioner)

f: a vacuum fitting g: a spring for raising the central body after actuation so as to permit the easy positioning and removal of the dishes or plates h: a handle for locking and unlocking the central body in order to remove it when necessary i: a support shaft for the central body lowering and raising means l: a ball-grip actuating lever with an arm for releasing the cover to allow cleaning of the aspiration cylinder m: a ball-grip carrying the cover-release rod.

As will be apparent to persons of ordinary skill in the art, many components of the apparatus according to the invention that has been illustrated above by way of example can be replaced by functionally equivalent component parts. For example, the mechanical spring heretofore described can be replaced by any equivalent technical means, such as a hydraulic or pneumatic means.

The lowering arm is likewise simply a convenient means for embodiments of the apparatus suitable for use on a small scale, while other equivalent systems can fulfill the same function and may also prove preferably when the apparatus is used on an industrial scale, as for example when the number of operations repeated daily is such as to require an electronically controlled system for actuating a device for lowering the central body and returning it to a raised position above the baseplate of said body through the intermediary of a motor. In such a case, the operation of positioning the dish or plate and of collecting the treated plates is preferably automated and controlled by an electronic system.

The dish or plate positioner (of which an example is shown in FIG. 4A detail 4d) facilitates the centering of the dish or plate in the correct position so that the position of the wells is pre-established. The dimension and form of the dish or plate positioner naturally depend on the dimension and form of the dish or plate employed. Preferably, said positioner is constructed from plastic materials or metal, and is secured to the baseplate and/or support shaft in such a manner as to allow the plate to be suitably replaced as needed.

For embodiments of the apparatus of the invention intended for the treatment of a given type of dish or plate, said positioner can also be fixed to the baseplate instead of being removable.

As stated previously, the number of wells and their size depend not only on the size of the dish or plate, but also on the specific use for which the dish or plate is intended, and, ultimately, on the amounts and the diffusion properties of the used reagents.

For circular dishes or plates it is generally preferable to bore a single series of wells along the circumference at a sufficient distance from the edge, so that the central body will also be such as to carry the hollow borers arranged along a circumference (an example is shown in FIG. 2). If the specific application so requires, provision can be made for a central well or a more inwardly positioned circle of wells, or for any other arrangement, with appropriate modification of the geometry of the central body and the disposition of the hollow borers in it. In the case of square dishes or plates, it is generally preferred to operate with wells disposed in several rows. In such a case, the central body will carry the hollow borers disposed in rows instead of in circles.

The dimensions of the dishes or plates suitable for treatment using the apparatus of the invention vary, and include those available on the market.

Examples of dishes or plates are circular dishes or plates having a diameter of from 35 mm to 145 mm, and square dishes or plates having sides of length ranging from 100 mm to 230 mm.

Square dishes or plates with a size larger than, but multiples of, the size of the central body or an apparatus of the invention can also be treated by successively positioning them under said apparatus of the invention.

We claim:

1. An apparatus for simultaneously forming a desired number of wells in dishes or plates containing a gelatinous matrix consisting of:
   a) a central body which contains an internal cavity;
   b) a preselected number of hollow stainless steel borers which are suitably shaped at the distal portion of said borer so as to bore out a well in said gelatinous matrix without leaving gelatinous residue on the bottom of the plate, and where said borers are at predetermined dimensions and at a predetermined distance one from the other in relation to the wells to be formed in the gelatinous matrix, and wherein said hollow borers are immovably affixed to the central body in such a manner that the proximal portions of said hollow borers debouch into said internal cavity of said central body;
   c) means for aspirating said agar plugs into said internal cavity from said hollow borers;
   d) a baseplate;
   e) means for connecting said baseplate to said central body, thereby providing support for said central body;
   f) means for positioning said plate or said dish on said baseplate, suitable to keep said plate or dish stationary during said well forming operation;
   g) means for lowering said hollow borers towards said stationary dish or plate, thereby allowing said hollow borers to penetrate said gelatinous matrix contained within said dish or plate without any motion substantially perpendicular to the path of penetration of the borers to the gel; and
   h) means for raising said hollow borers away from said dish or plate without any motion substantially perpendicular to the path of penetration of the borers to the gel after said penetration.

2. An apparatus as described in claim 1, wherein the matrix contained in the dish or plate is agar-based.

* * * * *